United States Patent [19]

Szczepanski

[11] Patent Number: 5,752,790
[45] Date of Patent: May 19, 1998

[54] METHOD AND APPARATUS FOR DETERMINING THE SUITABILITY OF WORKPIECES FOR MACHINING

[75] Inventor: Thomas L. Szczepanski, Penfield, N.Y.

[73] Assignee: The Gleason Works, Rochester, N.Y.

[21] Appl. No.: 399,661

[22] Filed: Mar. 7, 1995

[51] Int. Cl.⁶ .................................................. B23F 17/00
[52] U.S. Cl. ............................ 409/2; 451/5; 409/84
[58] Field of Search .............................. 409/2, 51, 80, 409/84, 131, 133, 149, 195; 408/2; 451/47, 8, 78, 5

[56] References Cited

U.S. PATENT DOCUMENTS

| | | | |
|---|---|---|---|
| 3,932,053 | 1/1976 | Hack | 409/84 X |
| 4,790,697 | 12/1988 | Hines et al. | 408/2 X |
| 4,981,402 | 1/1991 | Krenzer et al. | 409/26 |
| 5,059,905 | 10/1991 | Drits | 324/233 |
| 5,136,522 | 8/1992 | Leohrke | 451/5 X |
| 5,271,187 | 12/1993 | Yoneda et al. | 451/5 X |
| 5,315,789 | 5/1994 | Takashi | 451/5 |
| 5,419,222 | 5/1995 | Bieg | 409/133 X |

FOREIGN PATENT DOCUMENTS

| | | |
|---|---|---|
| 0348606 | 1/1990 | European Pat. Off. |
| 2847452 | 5/1980 | Germany ............... 409/133 |
| 2141365 | 12/1984 | United Kingdom ...... 409/133 |
| 8500428 | 1/1985 | WIPO . |

*Primary Examiner*—M. Rachuba
*Assistant Examiner*—Henry Tsai
*Attorney, Agent, or Firm*—Robert L. McDowell; Ralph E. Harper

[57] ABSTRACT

A method for determining the suitability of workpieces for machining. A workpiece is probed with a non-contact type sensor to produce a voltage reading corresponding to the mass of the workpiece. The reading is compared to a tolerance voltage range based on the mass of a reference workpiece and from this comparison it is determined whether the workpiece is an uncut or cut workpiece and if it is appropriate to machine the workpiece.

15 Claims, 3 Drawing Sheets

METHOD AND APPARATUS FOR DETERMINING THE SUITABILITY OF WORKPIECES FOR MACHINING

FIELD OF THE INVENTION

The present invention is directed to the machining of workpieces, and specifically to detecting incorrect workpieces prior to a machining process.

BACKGROUND OF THE INVENTION

In the production of machined articles, particularly tooth articles such as gears, couplings, splines, and the like, it is now commonplace to utilize automated production systems.

In these automated systems it is not unusual for one or more machine tools to operate for extended periods of time with no operator present, the machines relying on their programmed computer-controlled cycles as well as automatic loading and transfer mechanisms to repeatedly machine large numbers of workpieces.

In some instances, such as a loader or transfer means malfunction especially in the absence of an operator, situations have arisen where a previously cut workpiece is once again loaded into a cutting machine or a gear blank is loaded into a grinding machine. In either case, the part is certainly destroyed and there is a distinct possibility that the tool and/or the machine itself will incur significant damage.

It is known to utilize a mechanical apparatus to check for correct workpieces prior to machining. One such apparatus comprises toothed wheel which contacts the appropriate surface of a work gear where tooth slots would be found. If the toothed wheel meshes with the work gear, and the particular machining process is cutting, the motion of the toothed wheel as it falls into mesh with the work gear activates a contact switch which alerts the operator or shuts the machine down since damage will occur if an attempt is made to cut the toothed work gear again.

On the other hand, a similar toothed wheel may also be used to indicate an incorrect work gear for a grinding process. In this case, if the toothed wheel does not mesh with the work gear, the toothed wheel is essentially pushed away from the work gear thereby activating a contact switch to alert the operator or shut off the grinding machine.

Mechanical systems have shown themselves not to be particularly well adaptable to automated production environments. Mechanical mechanisms tend to be cumbersome, can be disruptive to the flow of workpieces on a conveyor, and generally comprise many small components which increase the chances of breakdown and lengthy repair.

It is an object of the present invention to provide a method of determining the suitability of parts loaded onto a machine tool.

It is a further object of the present invention to provide a method of probing a workpiece prior to being loaded onto a machine tool to determine if the workpiece is correct for the machining operation of the particular machine.

SUMMARY OF THE INVENTION

The present invention is directed to a method of determining the suitability of a workpiece for machining. In particular the present method is one which prevents an incorrect workpiece from entering a machine tool.

For cutting processes, the inventive method comprises providing a non-contact sensor having a sensing face. A first value representative of the mass of one of a cut or uncut workpiece is also provided. A tolerance range with respect to the first value is determined.

A workpiece is positioned relative to the sensor whereby a surface of the workpiece is located in a defined spatial relationship with respect to the sensing face of the sensor. The workpiece surface is scanned with the sensor to produce a signal having a second value representative of the mass of the workpiece.

The second value is compared to the tolerance range and, (a) if the first value is based on a cut workpiece: the workpiece is machined if the second value is outside of the tolerance range, or, the workpiece is rejected if the second value is within the tolerance range, or, (b) if the first value is based on an uncut workpiece: the workpiece is rejected if the second value is outside of the tolerance range, or, the workpiece is machined if the second value is within the tolerance range.

If the machining process is a grinding process for previously cut parts, the above-described process also applies except that in part (a) when the first value is based on a cut workpiece:

the workpiece is rejected if the second value is outside of the tolerance range, or, the workpiece is machined if the second value is within the tolerance range, or, (b) when the first value is based on an uncut workpiece: the workpiece is machined if the second value is outside of the tolerance range, or, the workpiece is rejected if the second value is within the tolerance range.

DETAILED DESCRIPTION OF THE PREFERRED EMBODIMENT

The present invention will now be discussed with reference to the preferred embodiments and the drawings.

Figure 1:
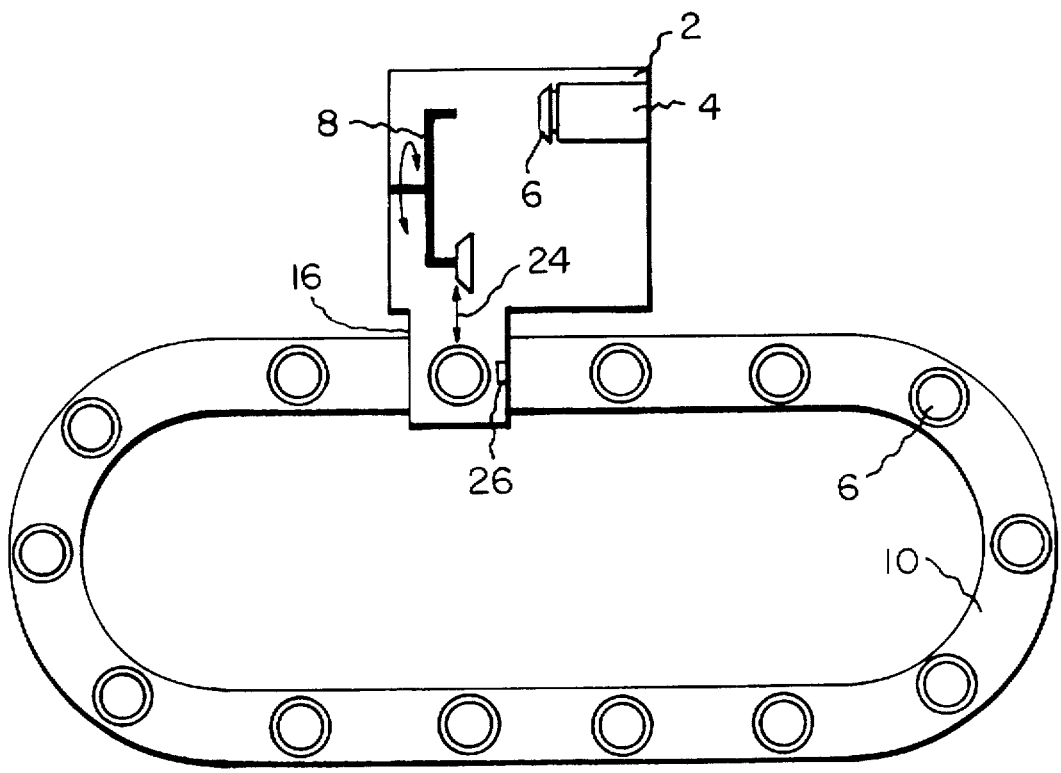
FIG. 1 is a schematic top view of a cutting machine, workpiece conveying mechanism, and transfer mechanism.

FIG. 1 schematically illustrates a machine tool 2, such as a computer numerically controlled gear cutting or grinding machine, having a work holding means 4 for releasably mounting a workpiece 6, for example, a bevel gear. Such machines are well known in the art and an example of one type may be found in U.S. Pat. No. 4,981,402 to Krenzer et al. The machine tool also includes an appropriate tool, such as a cutting tool or grinding wheel, which is well known in the art has been omitted for the sake of enhanced clarity in illustrating the present invention. The machine 2 also includes a delivery means such as a rotatable gripper arm 8 to automatically deliver workpieces to and remove workpieces from the work spindle 4.

Workpieces 6 may be delivered to and removed from the machine 2 via a conveyor 10. The illustrated conveyor 10 is a loop-type conveyor although the conveyor may be of any shape and may include an inlet for receiving workpieces and an outlet for transporting machined workpieces to another area for storage or further processing. In loop-type conveyors, an operator loads workpieces to and unloads workpieces from the conveyor.

Workpieces 6 are transferred between the conveyor 10 and machine 2 by a transfer means 16. In the exemplary embodiment shown by FIG. 2, a workpiece 6 is first lifted from its position 20 on conveyor workpiece support 12 to a predetermined height at position 21 and then the workpiece is carried through an arc of about ninety (90) degrees to position 22. From position 22, workpiece 6 is transported into machine 2 (see arrow 24) and gripped by the gripper arm 8. The gripper arm 8 then rotates and delivers the workpiece to the machine spindle 4. The reverse of this procedure is followed to transfer a workpiece from the machine spindle to the conveyor 10. Means to effect transfer from a conveyor to a machine tool are numerous and are well known in the art and are believed to be well understood by the skilled artisan.

Situations periodically arise where an operator is detained away from the machine for longer than expected durations, or, mechanical failure prevents workpieces from being automatically removed from the conveyor. In these instances, workpieces leaving the machine 2 on conveyor 10 may not removed from the conveyor 10 before they are transported around again to the transfer mechanism 16 and hence are reintroduced into the machine 2. Also, an incorrect workpiece may be placed on the conveyor either by the operator or as one of a batch of parts being automatically loaded.

If any of these instances occur, the workpiece will certainly be destroyed if an attempt is made to machine the workpiece a second time. There is great risk to the cutting tool as well as the machine itself and anyone near the machine is placed in danger due to metal or grinding wheel fragments which may be propelled away from the cutting or grinding areas.

Therefore, in cutting processes it is desirable to prevent reintroduction of already cut workpieces into the cutting machine while in grinding processes it is necessary to prevent the introduction of workpiece blanks into the grinding machine. In either type of process, it is desirable to prevent the machining of any part other than that specifically intended to be machined.

The present invention comprises a method of determining the suitability of a part to be machined. In the inventive method a workpiece is probed by a non-contact type probe which provides a signal value representative of the physical characteristics of the workpiece. Once such a signal value is determined, it is compared with a value representative of a desired, or undesired, workpiece for the particular machining operation.

Figure 3:
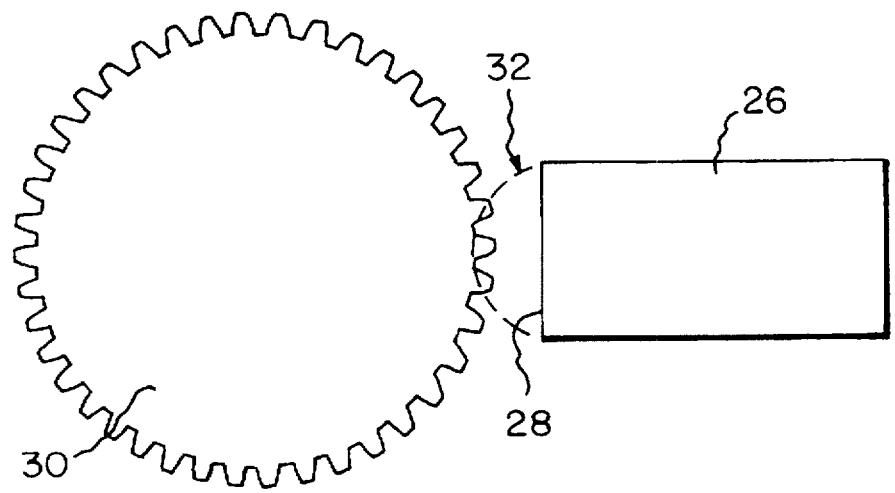
FIG. 3 illustrates a top view of a cut gear adjacent the non-contact sensor of the inventive method.
Figure 4:
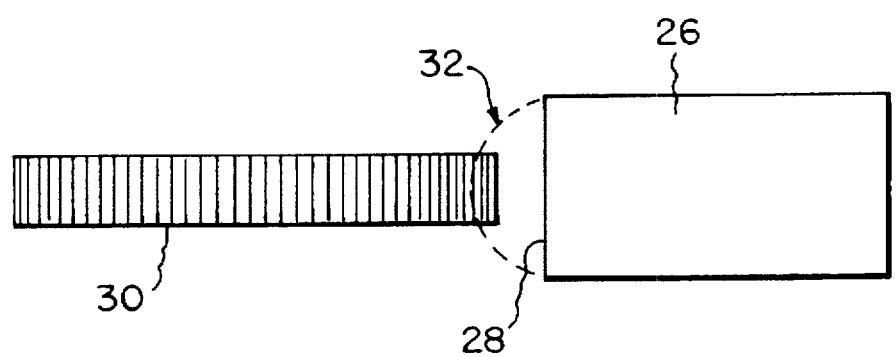
FIG. 4 illustrates a side view of a cut gear adjacent the non-contact sensor of the inventive method.

FIG. 3 illustrates a preferred embodiment wherein a non-contact type probe or sensor 26 having a sensing face 28, preferably a circular sensing face, is placed adjacent a workpiece which in this example is a spur gear 30 which is shown in top view. The probe preferably is of the inductance type and produces a low level radio frequency field 32. This type of non-contact type probe is itself known. FIG. 4 illustrates an arrangement similar to FIG. 3 except that spur gear 30 is shown in side view.

Any metal that enters the field 32 will cause energy loss in the internal oscillator of the probe 26 due to generated eddy currents. This energy loss is converted into a linear analog output signal that is proportional to the distance from the sensing face 28 to the target which in FIG. 3 is spur gear 30.

As stated above, the energy loss variations which result from the changes in the sensing face to target distance are caused by the eddy currents losses in the target material. However, the magnitude of these losses are dependent upon several factors: conductivity and mass of the target, distance to the target, and shape of the target.

The effect of distance and shape have on the target can be reduced by preferably having the sensing face diameter larger than the target size and thereby reduce the magnitude of those losses due to the distance and shape of the target.

With regard to the conductivity and mass of the target gear, the conductivity is consistent from gear to gear because of the similarity of the metal composition and can effectively be canceled out. However, the mass of the gear will vary depending if it is cut or uncut, thus causing a large energy variation. This energy variation, when converted into a linear analog output signal, is a signal representative of a cut part, in the case of spur gear 30 in FIGS. 3 or 4, and can be used to detect cut or uncut parts.

Figure 2:
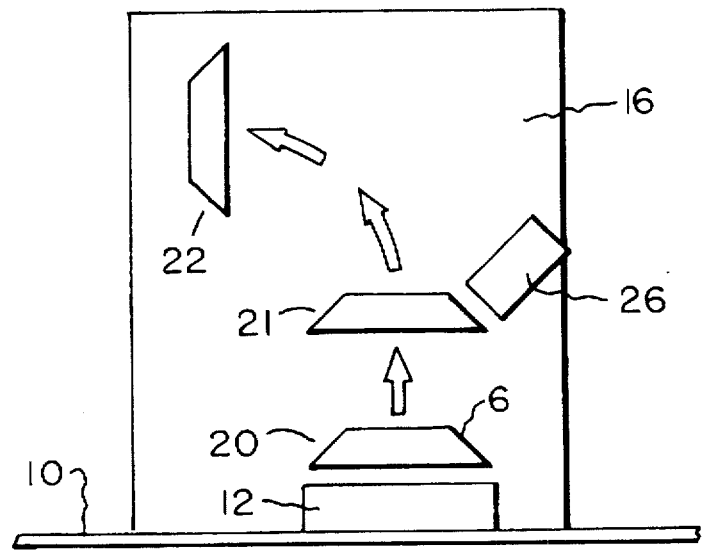
FIG. 2 is a front view of the transfer mechanism schematically illustrating placement of the non-contact sensor of the present invention.

Looking again at FIGS. 1 and 2, it can be seen that bevel gear blanks 6 may be probed to determine their suitability for machining in cutting machine 2. The probe 26 may be placed at any convenient location prior to introducing the gear blanks 6 into the machine 2. In this example, probe 26 is mounted to transfer means 16. As the workpiece 6 is raised from the conveyor support 12 it is brought to position 21 prior to being transported along the arc-shaped path to position 22. At position 21, the surface of the workpiece 6 to be machined is adjacent the sensing face of probe 26 and is scanned (i.e probed) to determine a value representing the mass of workpiece 6.

Although placement of the probe 26 is shown at a location where the workpiece 6 is probed while stationary, it is to be understood that the present invention also contemplates probing of workpieces while in motion, such as moving along conveyor 10. In that instance, probe 26 would be mounted at a desired location along conveyor 10.

Figure 5:
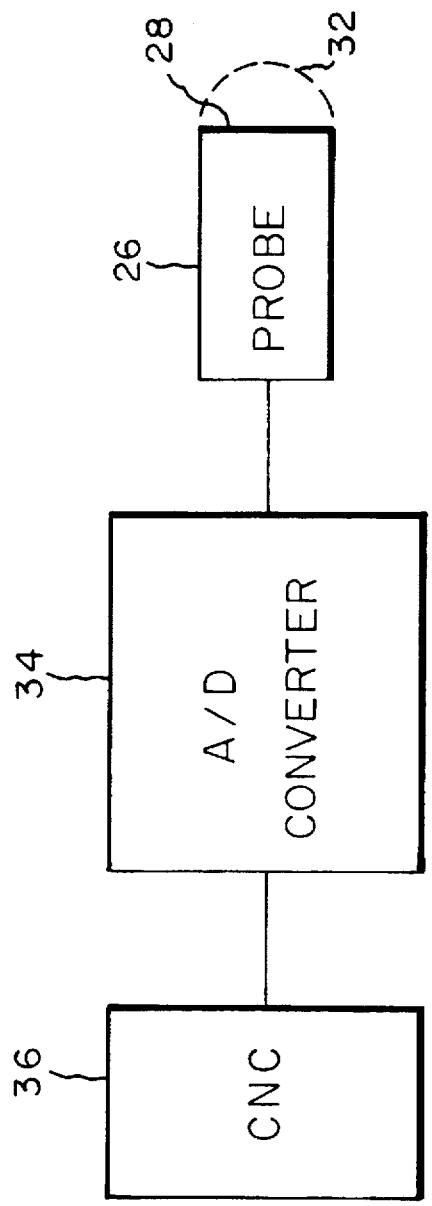
FIG. 5 is a block diagram showing the components of the scanning system of the present invention.

Once an analog signal has been generated by the probe 26, it is converted to a digital value and sent to the controller of the machine tool 2 where it is compared to a stored reference value. FIG. 5 shows a block circuit diagram of the preferred arrangement comprising probe 26, analog-to-digital converter 34, and computer numerical control (CNC) 36.

The probe 26 may be any type of non-contact gauging sensor such as Model PA232WF by Electro having an analog output of 0–10 volts DC. The analog-to-digital converter 34 preferably is of the type manufactured by Phoenix Contact USA, Model MCR-ADC12/U-10/BUS having a 24 volt DC digital output. The computer numerical control unit 36 is preferably of the type manufactured by GE Fanuc, Model 15MA or 15MB.

As mentioned above, a reference value is provided to the computer. This reference value is indicative of the mass of a particular cut or uncut workpiece. Actually, any number of cut and/or uncut workpiece values may be entered into the computer and the desired values simply recalled depending upon a particular workpiece to be machined. Reference values may also be supplied to the computer by scanning a workpiece, either cut or uncut, of the type to be machined. It must be mentioned that within the context of the present invention, the term "uncut workpiece" is intended to refer to a workpiece blank (e.g. gear blank) and the term "cut workpiece" is intended to refer to a machined article (e.g. a toothed gear or pinion member).

As an example, an uncut bevel gear blank made of 8620 steel and having a diameter of 8 inches (203.2 mm) was scanned by probe 26, as shown in FIG. 2, at the sensing face-to-target distances set forth in the table below and the voltage readings of the probe 26 were recorded. The uncut gear blank was then cut and scanned again at the same distances to obtain the voltage readings indicative of the mass after cutting.

| Distance - inches (mm) | Uncut Gear Blank (V) | Cut Gear (V) |
| --- | --- | --- |
| 0.150 (3.81 mm) | 3.16 | 4.86 |
| 0.175 (4.45 mm) | 3.81 | 5.55 |
| 0.200 (5.08 mm) | 4.44 | 6.23 |

As can be seen from the Table above, a significant voltage difference exists between the uncut gear and the cut gear. With this information, the reference value may be selected. It must be emphasized that regardless of the reference value or values selected, it is important that the same probing distance relied upon to acquire the reference data also be used when scanning the workpieces prior to machining in order to render comparisons valid.

If the voltage values obtained at a probing distance of 0.150 inch (3.81 mm), which is preferred, are used for comparison values, these voltage readings would be stored in the computer and when a workpiece was probed, the voltage value of that probed workpiece would be compared with the stored value. It is immaterial which value, uncut or cut, is selected as a reference value as long as the proper comparison is made. It should be understood that not all uncut or cut parts will register exactly the same voltage value as the reference value and, taking this into consideration, a tolerance range is preferably determined with respect to the reference value.

The tolerance range preferably is about plus or minus 10% (i.e. +/– 10%) of the chosen reference value. Using 3.16 as a reference value would yield a tolerance range of 2.85–3.48 volts. As a matter of caution, it may be desirable to first determine the difference between the uncut and cut voltage values for a particular workpiece to be sure that the +/– difference (e.g. +/– 10%) will not create a tolerance range for one of the values that actually overlaps or comes very close to the value not selected as a reference. If that situation occurs, a smaller +/– percentage should be selected. As an alternative to assigning a +/– percentage amount, a defined difference may also be assigned such as +/– 0.25 volt.

For example, if the uncut value of 3.16 was selected as a reference value. The uncut bevel workpieces 6 in FIG. 1 would be also probed at a distance of 0.150 inch (3.81 mm) and their respective values compared with the tolerance range of 2.85–3.48 volts. As long as the probed voltage values from the workpieces 6 were each within the above tolerance range, the respective workpieces would be cut on machine 2. However, if one of the workpieces were a cut gear of the same size, the voltage reading from probe 26 in FIGS. 1 or 2 would be about 4.86 volts as can be seen from the Table. In this instance, the actual reading would be outside the tolerance range and the workpiece would be rejected. Rejecting the workpiece could be accomplished in many ways such as stopping the machining process or placing the part back on the conveyor and continuing on to the next workpiece.

The reference value based on a cut gear could also be used in the cutting process discussed above. In this case, the cut gear reference value of 4.86 volts would yield a tolerance range of 4.37–5.35 volts based on +/– 10%. The computer would be instructed to permit cutting of workpieces whose probed values were outside of the tolerance range and to reject any workpiece having a probed value within the tolerance range since the tolerance range represents a cut gear. If a cut gear were on the conveyor prior to being machined, the probed value would be within the tolerance range since the range was based on a cut gear and the workpiece would be rejected.

It can be seen that the present invention is also applicable to finishing processes (such as grinding, skiving, honing, or lapping) for rough-cut articles. Referring to the above Table, reference values for either cut or uncut gears would be compared to the actual workpieces to be machined. For example, it is usually a cut gear that is ground and the voltage value indicative of the cut gear (4.86 volts at a distance of 0.150 inch) would be compared to the reference value tolerance range. If the tolerance range (at +/– 10%) were based on a cut gear (4.37–5.35 V), the actual value of 4.86 V would be within the tolerance range and the gear would be ground. If, however, the workpiece on the conveyor were a gear blank, the voltage reading would be considerably lower (3.16 V) and therefore outside of the tolerance range established for a cut gear. The part would then be rejected.

Of course, a tolerance range based on a gear blank could be utilized and then any gears having voltage values outside the tolerance range would be ground and those having a probed value within the range would be rejected since this would be indicative of a gear blank which would cause great damage if grinding were attempted.

It is to be understood that while the present invention has been discussed with reference to cut and uncut gears, the inventive detecting method is also capable of detecting workpieces which are unsuitable for machining because of size, type, or composition or any other variable which affects the mass of the workpiece and thus lends itself to being detected by the inventive process.

While the invention has been described with reference to preferred embodiments it is to be understood that the invention is not limited to the particulars thereof. The present invention is intended to include modifications which would be apparent to those skilled in the art to which the subject matter pertains without deviating from the spirit and scope of the appended claims.

What is claimed is:

1. A method of detecting a cut or uncut workpiece prior to cutting to produce a toothed article, said method comprising:

providing a non-contact sensor having a sensing face, providing a first value representative of the mass of an uncut workpiece, determining a tolerance range with respect to said first value, positioning said workpiece relative to said sensor whereby a surface of said workpiece is located in a defined spatial relationship with respect to said sensing face of said sensor, scanning said workpiece surface with said sensor to produce a signal having a second value representative of the mass of said workpiece, comparing said second value to said tolerance range, and, rejecting said workpiece if said second value is outside of said tolerance range, or, cutting said workpiece to form said tooth article if said second value is within said tolerance range.

2. The method of claim 1 wherein said workpiece is rejected when said second value is greater than said tolerance range.

3. A method of determining the suitability of a workpiece for a cutting operation, said method comprising:

providing a non-contact sensor having a sensing face, providing a first value representative of the mass of one of a cut or uncut workpiece, determining a tolerance range with respect to said first value, positioning said workpiece relative to said sensor whereby a surface of said workpiece is located in a defined spatial relationship with respect to said sensing face of said sensor, probing said workpiece surface with said sensor to produce a signal having a second value representative of the mass of said workpiece, comparing said second value to said tolerance range, and, (a) if said first value is based on said cut workpiece:
rejecting said workpiece if said second value is within said tolerance range, or, machining said workpiece if said second value is outside of said tolerance range, or, (b) if said first value is based on said uncut workpiece:
machining said workpiece if said second value is within said tolerance range, or, rejecting said workpiece if said second value is outside of said tolerance range.

4. The method of claim 3 wherein said first value is provided by scanning a corresponding surface of said cut or uncut workpiece with said sensor and said corresponding surface being in the same said defined spatial relationship.

5. The method of claim 3 wherein said non-contact sensor is an inductive sensor and said first and second values are voltage values.

6. The method of claim 3 wherein said defined spatial relationship comprises positioning said surface of said workpiece at about 0.150 inches from said sensing face of said sensor.

7. The method of claim 3 wherein said sensing face is circular and comprises a diameter greater than the size of said workpiece surface being probed.

8. A method of determining the suitability of a workpiece prior to a finish machining process for toothed articles, said method comprising:

providing a non-contact sensor having a sensing face, providing a first value representative of the mass of one of a cut or uncut workpiece, determining a tolerance range with respect to said first value, positioning said workpiece relative to said sensor whereby a surface of said workpiece is located in a defined spatial relationship with respect to said sensing face of said sensor, scanning said workpiece surface with said sensor to produce a signal having a second value representative of the mass of said workpiece, comparing said second value to said tolerance range, and, (a) if said first value is based on said cut workpiece:
finish machining said workpiece if said second value is within said tolerance range, or, rejecting said workpiece if said second value is outside of said tolerance range, or, (b) if said first value is based on said uncut workpiece:
rejecting said workpiece if said second value is within said tolerance range, or, finish machining said workpiece if said second value is outside of said tolerance range.

9. The method of claim 8 wherein said finish machining comprises grinding.

10. The method of claim 8 wherein said first value is provided by scanning a corresponding surface of said cut or uncut workpiece with said sensor and said corresponding surface being in the same said defined spatial relationship.

11. The method of claim 8 wherein said non-contact sensor is an inductive sensor and said first and second values are voltage values.

12. The method of claim 8 wherein said defined spatial relationship comprises positioning said surface of said workpiece at about 0.150 inches from said sensing face of said sensor.

13. The method of claim 8 wherein said sensing face is circular and comprises a diameter greater than the size of said workpiece surface being probed.

14. The method of claim 8 wherein said uncut workpiece is a gear blank.

15. In combination with a computer controlled machine tool for machining gears and the like:

a system for detecting the suitability of gears-type workpieces to be machined, said system comprising:

a non-contact probe communicating with said computer, said probe being positionable adjacent the machining surface of said gear-type workpiece to be machined on said machine tool and producing an output signal value indicative of the mass of said workpiece, said computer including stored values indicative of the mass of said workpiece in at least one of an uncut condition and a cut condition, said values being of the same type as said output signal value of said probe, said computer comparing said output signal value with a predetermined range based on said at least one of said stored values to determine if said output signal value is within said predetermined range, said computer being programmed to identify said predetermined range as an acceptable range and thereby permit machining of said workpiece if said output signal value is within said range, or, said computer being programmed to identify said predetermined range as an unacceptable range and thereby terminate machining of said workpiece.

* * * * *